United States Patent [19]

Finke et al.

[11] 3,962,378

[45] June 8, 1976

[54] PREPARATION OF PHOSPHORUS-ORGANIC ESTERS

[75] Inventors: Manfred Finke, Fischbach, Taunus; Hans-Jerg Kleiner, Bad Soden, Taunus, all of Germany

[73] Assignee: Hoechst Aktiengesellschaft, Frankfurt am Main, Germany

[22] Filed: July 8, 1974

[21] Appl. No.: 486,315

[30] Foreign Application Priority Data

July 14, 1973 Germany............................ 2335852

[52] U.S. Cl............................. 260/968; 260/491; 260/953; 260/982
[51] Int. Cl.²......................... C07F 9/32; C07F 9/40
[58] Field of Search.................... 260/968, 982, 953

[56] References Cited
UNITED STATES PATENTS

| | | | |
|---|---|---|---|
| 2,864,848 | 12/1958 | McArthur............................ | 260/968 |
| 2,934,555 | 4/1960 | O'Brien et al.................. | 260/968 X |
| 3,155,639 | 11/1964 | Emmons et al.................. | 260/968 X |

OTHER PUBLICATIONS

Wagner et al., *Synthetic Organic Chemistry*, John Wiley & Sons (New York) 1953, p. 486.

*Primary Examiner*—Richard L. Raymond
*Attorney, Agent, or Firm*—Curtis, Morris & Safford

[57] ABSTRACT

2-Hydroxyethane-phosphonic acid diesters, 2-hydroxyethylphoshinic acid esters and the corresponding thiophoshonic acid-O,O-diesters or thiophosphinic acid-O-esters of the formula

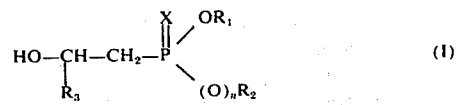

wherein $R_1$ is alkyl having from 1 to 18 carbon atoms,
$R_2$ has the meaning of $R_1$ or represents cycloalkyl having up to 10 carbon atoms, alkenyl having up to 18 carbon atoms, aryl having up to 14 carbon atoms or aralkyl having up to 15 carbon atoms,
$R_3$ means hydrogen, alkyl having up to 18 carbon atoms, alkenyl having up to 18 carbon atoms, cycloalkyl having up to 10 carbon atoms, aryl having up to 14 carbon atoms or aralkyl having up to 15 carbon atoms, the substituents $R_1$–$R_3$ optionally being substituted, X represents oxygen or sulfur and n represents either 0 or 1, are prepared from 2-acyloxyethane-phosphonic acid diesters, 2-acyloxy-ethyl-phoshinic acid esters or the corresponding thiophoshonic acid-O,O-diesters or thiophoshinic acid-O-esters and are important intermediate products for the preparation of plant protecting agents and flame-proofing agents.

15 Claims, No Drawings

PREPARATION OF PHOSPHORUS-ORGANIC ESTERS

The preparation of 2-hydroxyethane-phosphonic acid dialkyl esters from phosphorous acid dialkyl esters and ethylene oxide at 130°C under pressure in the presence of acid catalysts is well known (Houben-Weyl, 4th edit., vol. XII/1, pg. 459, 1963; A.N. Pudovik, B. E. Ivanov, Izv. Akad. S.S.S.R. 1952, 947). According to this process the dimethyl and diethyl ester of 2-hydroxyethane phosphonic acid are obtained in an approx. 20% yield, whilst according to this same literature reference phosphorous acid dibutyl ester does not react under pressure, even at 160°–170°C.

It is also possible to prepare 2-hydroxyethane phosphonic acid dialkyl esters by reacting the sodium salts of phosphorous acid dialkyl esters with ethylene oxide and subsequent decomposition of the primarily formed reaction product with acetic acid (G. V. Chelintsev, V. K. Kuskov, Z. obsc. Chim. 16, 1481 (1946): N. Kreuzkamp, *Naturwissenschaften* 43, 81 (1956)). However, this reaction gives even poorer yields than those obtained by acid-catalyzed reaction of the free phosphonic acid diesters with ethylene oxide. Besides, it requires molar quantities of sodium and acetic acid (Houben-Weyl, 4th edit., vol. XII/1, pg. 459, 1963).

It is also known that 2-hydroxyethane-phosphonic acid diethyl ester is formed in extremely low yields upon reacting 2-chloro-ethanol with the sodium salt of phosphorous acid diethyl ester (J. Songstad, *Acta chem. Scand*, 21, 1681 (1967). The author assumes that hydroxyalkane-phosphonic acid diesters have a tendency to cyclization and polymerization and therefore cannot be considered as stable compounds.

It has now been found that it is possible to obtain 2-hydroxyethane-phosphonic acid diesters, 2-hydroxyethyl phosphinic acid esters and the corresponding thiophosphonic acid-O, O-diesters or thiophosphinic acid-O-esters having the formula (I)

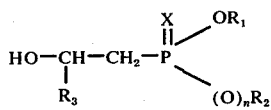

(I)

wherein $R_1$ represents an optionally substituted alkyl group having up to 18 carbon atoms, preferably from 1 to 12, especially from 1 to 4 carbon atoms which may be substituted by halogen, especially by chlorine, $R_2$ has the meaning of $R_1$ or represents cycloalkyl having up to 10 carbon atoms, especially cyclohexyl, alkenyl having up to 18 carbon atoms, preferably up to 12, especially up to 4 carbon atoms, aryl having up to 14 carbon atoms, especially phenyl, aralkyl having up to 15 carbon atoms, especially benzyl, which may optionally be substituted, $R_3$ is hydrogen, an alkyl group or an alkenyl group having up to 18 carbon atoms, especially methyl, a cycloalkyl group having up to 10 carbon atoms, especially cyclohexyl, an aryl group having up to 14 carbon atoms, especially phenyl, an aralkyl group having up to 15 carbon atoms, especially benzyl, which may optionally be substituted, X is oxygen or sulfur and $n$ represents 0 or 1, by heating 2-acyloxyethanephosphonic acid diesters, 2-acyloxyethyl-phosphinic acid esters or the corresponding thiophosphonic acid-O,O-diesters or thiophosphinic acid-O-esters having the general formula (II)

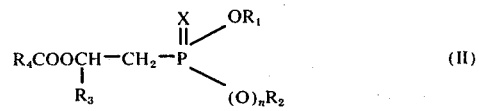

(II)

wherein $R_1$, $R_2$, $R_3$, X and $n$ have the aforesaid meanings and $R_4$ stands for an alkyl group having from 1 to 4 carbon atoms, especially for a methyl group, diluted in an alcohol ROH having from 1 to 4 carbon atoms, especially methanol or ethanol, to a temperature of from 25° to 150°C, preferably from 40° to 120°C, especially from 60° to 90°C, while adding from 0.1 to 25 mol %, preferably from 0.5 to 15 mol % and especially from 1 to 8 mol %, of a strong acid, or from 1 to 15 mol %, preferably from 3 to 7 mol %, of a strong base, and eliminating the carboxylic acid ester $R_4COOR$ formed during this reaction continuously by distillation from the reaction mixture.

It is surprising that the phosphonic acid esters and phosphinic acid esters are not transesterified under these reaction conditions with the alcohol used or with the 2-hydroxyethyl group of the phosphonic acid ester and phosphinic acid ester formed during the reaction. Such a transesterification of phosphonic acid diesters with alcohols is known (Houben-Weyl, vol. XII/1, pg, 500, 1963); B. A. Arbusov, V. S. Vinogradova, Izv. Akad. S.S.S.R. 1952, 882; C.A. 47, 10 464 (1953)).

By the process of the present invention 2-hydroxyethane phosphonic acid diesters which could be obtained according to preparation methods known hitherto with poor yields only can now be obtained easily and in good to excellent yields. 2-hydroxyethane-phosphonic acid diesters — such as the novel 2-hydroxyethyl phosphinic acid esters, 2-hydroxyethane-thiophosphonic acid-O,O-diesters and 2-hydroxyethyl-thiophosphinic acid-O-esters - are stable compounds which do not show any tendency to cyclization or polycondensation.

Possible initial substances are 2-acyloxyethane-phosphonic acid diesters, such as for example 2-acetoxyethane-phosphonic acid dimethyl ester, 2-acetoxyethane-phosphonic acid diethyl ester, 2-acetoxyethane-phosphonic acid bis-(2-chloroethyl ester), 2-acetoxyethane-phosphonic acid diisopropyl ester, 2-acetoxyethane-phosphonic acid diisobutylester, 2-acetoxyethane-phosphonic acid didodecyl ester, 2-acetoxyethane-phosphonic acid dioctadecyl ester, 2-acetoxy-2-phenyl-ethane-phosphonic acid dimethyl ester and 2-acetoxy-2-phenyl-ethane-phosphonic acid diethyl ester, and the corresponding thiophosphonic acid-O,O-diesters, such as for example 2-acetoxyethane-thiophosphonic acid-O,O-dimethyl ester, 2-acetoxyethane-thiophosphonic acid-O,O-diethyl ester, 2-acetoxyethane-thiophosphonic acid-O,O-diisobutyl ester, 2-acetoxyethane-thiophosphonic-acid-O,O-didodecyl ester and 2-acetoxyethane-thiophosphonic acid dioctadecyl ester. Moreover, 2-acetoxyethyl-phosphinic acid esters can also be used as initial substances, for example (2-acetoxyethyl)-methyl phosphinic acid methyl ester, (2-acetoxyethyl)-methyl-phosphinic acid ethyl ester, (2-acetoxyethyl)-methyl-phosphinic acid 2-chloroethyl ester, (2-acetoxyethyl)-methyl-phosphinic acid isobutyl ester, (2-acetoxyethyl)-methylphosphinic acid dodecyl ester, (2-acetoxyethyl)-methyl-phosphinic acid octadecyl ester, (2-acetoxyethyl)-vinyl-phosphinic acid methyl ester, (2-acetoxyethyl)-phenyl-phosphinic acid isobutyl ester, (2-acetoxyethyl)-cyclopentyl-phosphinic acid isobutyl ester, (2-acetoxyethyl)-cyclopentyl-phosphinic acid isobutyl ester, (2-acetoxy-2-methylethyl)-methyl phosphinic acid isobutyl ester and (2-acetoxy-2-phenyl-ethyl)-phenyl-phosphinic acid isobutyl ester, as well as the corresponding thiophosphinic acid-O-esters, such as (2-acetoxy-ethyl)-methylthiophosphinic acid -O-methyl ester, (2-acetoxyethyl)-methylthiophosphinic acid-O-ethyl ester, (2-acetoxyethyl)-methyl-thiophosphinic acid-O-propyl ester, (2-acetoxyethyl)-methyl-thiophosphinic acid-O-butyl ester and (2-acetoxyethyl)-methyl-thiophosphinic acid-O-dodecyl ester.

Of course, higher 2-acyloxyethyl-derivatives may be used as initial substances as well, such as for example propanoyloxy-ethane phosphonic acid dimethylester, butanoyloxy-ethanephosphonic acid dimethyl ester, 2-acetoxyethane-phosphonic acid diester and 2-acetoxyethyl phosphinic acid ester, 2-acetoxyethane-thiophosphonic acid-(O,O)-diester and 2-acetoxyethylthiophosphinic acid-(O)-ester are preferred, however.

The initial substances are advantageously prepared according to German Offenlegungsschrift No. 2.127.821.

Base metals such as Li, Na, K, Ca, Mg, Al, their alcoholates, amides, hydrides, oxides and hydroxides such as $NaOCH_3$, $Mg(OC_2H_5)_2$, $Al(O-i-C_3H_7)_3$, $NaNH_2$, $NaH$, $CaH_2$, $CaO$, $BaO$, $NaOH$, $KOH$ are possible strongly basic catalysts. As acid catalysts may be used inorganic acids, such as for example HCl, HBr, HI, HF, $H_2SO_4$, $HClO_4$, $HNO_3$, $H_3PO_4$, $H_3PO_3$, $ClSO_3H$, and organic acids having a $p_{Ka}$-value below 2.5 such as for example dichloroacetic acid, trichloroacetic acid, trifluoroacetic acid and p-toluenesulfonic acid. As compared to basic catalysts, preference is given to acid catalysts.

The alcohols ROH being used as reaction components and as solvents may contain up to 4 carbon atoms, such as for example methanol, ethanol, propanol, butanol and isobutanol. Preference is given to methanol and ethanol, however. It is generally sufficient to use industrial grade alcohols. In the case of methyl esters of phosphonic acid phosphinic acids sensitive to hydrolysis, the yield of 2-hydroxyethyl-phosphonic acid derivatives or 2-hydroxyethyl-phosphinic acid derivatives can be improved by carrying out the reaction in anhydrous alcohol. The alcohol is used in 3-fold to 15-fold, preferably 6-fold to 12-fold, molar excess. Larger quantities of alcohols are possible, though they do not represent any technical interest.

Generally, the process according to the present invention is carried out in such a way that the 2-acyloxyethane-phosphonic acid diester, or 2-acyloxyethyl phosphinic acid ester, or 2-acyloxyethane thiophosphonic acid-(O,O)-diester, or 2-acyloxyethyl-thiophosphinic acid-(O)-ester is heated in excess alcohol ROH — while adding a strong base or acid — to a temperature of from 25°–150°C, preferably from 40°–120°C, especially from 60°–90°C, and subsequently the carboxylic acid alkyl ester $R_4COOR$ formed is slowly eliminated from the reaction mixture by distillation over a column together with part of the alcohol. Alcohols having from 1 to 4 carbon atoms form with almost all carboxylic acid alkyl esters azeotropic mixtures with minimum boiling points so that it is possible to eliminate by distillation the carboxylic acid alkyl ester from the reaction mixture even if the carboxylic acid ester has a higher boiling point than the alcohol used (Azeotropic Data, I, Advances in Chemistry Series No. 6, American Chemical Society, Washington 1952; Azeotropic Data II, Advances in Chemistry Series No. 35, American Chemical Society, Washington 1962).

It is also possible to eliminate the carboxylic acid esters from the reaction mixture by distillation under reduced pressure. In some cases it may be advantageous to replace part of the excess alcohol by addition of an inert solvent, such as for example benzene, toluene, chlorobenzene, xylene, dioxane, acetonitrile.

The reaction may also be performed in such a way that an alcoholic solution of the catalyst is added dropwise continuously during the reaction period. The reaction time is not a critical factor and, in many cases, varies from about 3 to 10 hours. The crude product is purified according to known methods, for example by distillation under reduced pressure, by extraction or by chromatography. The products thus purified are obtained in a yield of from about 70 to 95%.

The 2-hydroxyethane-phosphonic acid diesters, 2-hydroxyethyl-phosphinic acid esters or the corresponding thiophosphonic acid-O,O-diesters and thiophosphinic acid-O-esters prepared according to this process are important intermediate products for the preparation of plant protecting agents and flame-proofing agents. For example, copolymers of vinyl monomers with esters of acrylic acid or methacrylic acid and 2-hydroxyethane-phosphonic acid dialkyl esters have excellent flameretarding properties (Japanese, Pat. No. 71/20 823).

The following examples illustrate the invention:

EXAMPLE 1

2-hydroxyethane-phosphonic acid dimethyl ester 500 g of 2-acetoxyethane-phosphonic acid dimethyl ester are heated for 4 hours to 65°–70°C in 1 ltr. of methanol containing 0.5 weight percent of HCl. The methyl acetate formed is removed continuously from the reaction mixture by distillation, jointly with methanol. The reaction being terminated, the solvent is removed by distillation and the residue is fractionated under reduced pressure. 341 g of 2-hydroxyethane-phosphonic acid dimethyl ester (boiling point: 110°C/0.1 torr) (mm. Hg) are obtained, corresponding to a yield of 87% of the theoretical.

EXAMPLE 2

2-hydroxyethane-phosphonic acid dimethyl ester 600 g of 2-acetoxyethane-phosphonic acid dimethyl ester are heated for 5 hours to 65°–75°C in 600 ml of methanol to which 3 g of sodium had been added. A mixture of methyl acetate/methanol is removed continuously by distillation. The reaction being terminated, the residue is submitted to distillation under reduced pressure, 369 g of 2-hydroxyethane-phosphonic acid dimethyl ester (boiling point: 122°C/0.2 torr) are obtained, corresponding to a yield of 84% in the theoretical.

EXAMPLE 3

2-hydroxy-2-methylethane-phosphonic acid dimethyl ester 100 g of 2-acetoxy-2-methylethane-phosphonic acid dimethyl ester are heated for about 5 hours to 65°–75°C in 200 ml of methanol containing 1 wt.% of HCl. A mixture of methyl acetate/methanol is removed continuously by distillation over a column. The residue is fractionated in high vacuum. 60 g of 2-hydroxy-2-methyl-ethane-phosphonic acid dimethyl ester (b.p.: 125°–127°C/1.5 torr) are obtained, corresponding to a yield of 76% of the theoretical.

EXAMPLE 4

2-hydroxyethane-phosphonic acid diethyl ester 100 g of 2-acetoxyethane phosphonic acid diethyl ester are blended with 200 ml of methanol containing 1 wt.% of HCl and heated to 65°–70°C for 4 hours. A mixture of methyl acetate/methanol is removed continuously from the reaction mixture by distillation. Upon submitting the mixture of methyl acetate/methanol to gas chromatography no ethyl acetate at all and only traces of ethanol are found. The crude 2-hydroxyethanephosphonic acid diethyl ester is distilled under reduced pressure. 68 g of 2-hydroxyethane-phosphonic acid diethyl ester (b.p. 106°–109°C/0.1 torr) are obtained, corresponding to a yield of 83.5% of the theoretical.

EXAMPLE 5

2-hydroxyethane-phosphonic acid diethyl ester 100 g of 2-acetoxyethane phosphonic acid diethyl ester are blended with 200 ml of isobutyl alcohol containing 2 g of HCl and heated to 120°–150°C for 5 hours. A mixture of isobutyl acetate and isobutanol is removed continuously by distillation in the course of the reaction. By gas chromatography of the mixture of isobutyl acetate/isobutanol, no ethyl acetate and only traces of ethanol were found. 51 g of 2-hydroxyethanephosphonic acid diethyl ester are obtained after distillation under reduced pressure, corresponding to a yield of 62% of the theoretical.

EXAMPLE 6

2-hydroxyethane-phosphonic acid dimethyl ester

A solution of 50 g of 2-acetoxyethane-phosphonic acid dimethyl ester in 100 ml of anhydrous methanol is mixed with 0.5 g of KOH and heated to 65°–70°C for 5 hours while simultaneously removing a mixture of methyl acetate/methanol by distillation. The crude product is submitted to distillation under reduced pressure, 34 g of 2-hydroxyethane-phosphonic acid dimethyl ester are obtained, corresponding to a yield of 86.5% of the theoretical.

EXAMPLE 7

2-hydroxyethane-phosphonic acid dimethyl ester

A solution of 50 g of 2-acetoxyethane phosphonic acid dimethyl ester in 100 ml of anhydrous methanol is heated to 65°–70°C for 5 hours, while adding one drop of concentrated sulfuric acid. A mixture of methyl acetate/methanol is removed continuously by distillation in the course of the reaction. After a distillation under reduced pressure 33.5 g of 2-hydroxyethane-phosphonic acid dimethyl ester are obtained, corresponding to a yield of 85% of the theoretical.

EXAMPLE 8

2-hydroxyethane-phosphonic acid diethyl ester 100 g of 2-acetoxyethane phosphonic acid diethyl ester are heated to 80°C jointly with 200 ml of ethanol. To this solution are added dropwise within 5 hours 20 ml of ethanol containing 1 wt.% of $H_2SO_4$, while simultaneously removing by continuous distillation a mixture of ethylacetate and ethanol. The residue is submitted to distillation under reduced pressure. 64 g of 2-hydroxyethane-phosphonic acid diethyl ester are obtained, corresponding to a yield of 80% of the theoretical.

EXAMPLE 9

2-hydroxyethane-phosphonic acid dimethyl ester

A solution of 100 g of 2-acetoxyethane-phosphonic acid dimethyl ester in 100 ml of anhydrous methanol — 4 g of p-toluenesulfonic acid being added — is heated for 5 hours to 65°–75°C while removing simultaneously by distillation a mixture of methyl acetate/methanol. After distillation under reduced pressure, 59 g of 2-hydroxyethane-phosphonic acid dimethyl ester are obtained, corresponding to a yield of 75% of the theoretical.

EXAMPLE 10

2-hydroxyethyl-methyl-phosphinic acid isobutyl ester 200 g of acetoxyethyl-methyl-phosphinic acid isobutyl ester are heated to 65°–70°C in 400 ml of methanol containing 3 g of hydrogen chloride. The methyl acetate formed is removed slowly by distillation, jointly with methanol. The reaction being terminated, the solvent is eliminated under water jet vacuum and the residue submitted to distillation in high vacuum. 126.5 g of 2-hydroxyethyl-methyl-phosphinic acid isobutyl ester (b.p. 120°–125°C/0.2 torr) are obtained, corresponding to a yield of 78% of the theoretical.

EXAMPLE 11

2-hydroxyethyl-phenyl-phosphinic acid isobutyl ester 107 g of 2-acetoxyethyl-phenyl-phosphinic acid isobutyl ester (prepared according to German Offenlegungsschrift No. 2.127.821) are heated to 65°–70°C with 250 ml of methanol containing 2 g of HCl. The methyl acetate formed is removed continuously by distillation jointly with methanol. After distillation of the residue under reduced pressure, 77 g of 2-hydroxyethyl-phenyl phosphinic acid isobutyl ester (b.p. 160°C/0.9 torr) are obtained, corresponding to a yield of 84.5% of the theoretical.

EXAMPLE 12

2-hydroxyethyl-methyl-phosphinic acid-n-octyl ester 100 g of 2-acetoxyethyl-methyl phosphinic acid n-octyl ester are heated to 65°–70°C in 200 ml of methanol containing 0.5 wt.% of HCl, while simultaneously removing by distillation a mixture of methyl acetate/methanol. After distillation under reduced pressure 70 g of 2-hydroxyethyl-methyl-phosphinic acid-n-octyl ester (b.p. 139°C/0.2 torr) are obtained, corresponding to a yield of 82.5% of the theoretical.

EXAMPLE 13

2-hydroxyethane-thiophosphonic acid-O-O-diethyl ester 149 g of 2-acetoxyethane-thiophosphonic acid-O,O-diethyl ester (preparation according to German Offenlegungsschrift No. 2.127.821) are heated to 65°–70°C in 100 ml of methanol containing 3 wt.% of HCl, while removing simultaneously by distillation a mixture of methyl acetate/methanol. The reaction is terminated after approx. 5 hours. The residue is submitted to distillation under reduced pressure; 117 g of 2-hydroxyethanethiophosphonic acid-O,O-diethyl ester (b.p. 84°–88°C/0.1 torr) are obtained, corresponding to a yield of 95% of the theoretical.

EXAMPLE 14

2-hydroxyethyl-methyl-thiophosphinic acid-O-isobutyl ester 183 g of 2-acetoxyethyl-methyl thiophosphinic acid-O-isobutyl ester (preparation according to German Offenlegungsschrift No. 2.127.821) are heated for 4–5 hours to 65°–70°C, jointly with 100 g of methanol and 6 g of hydrogen chloride, while simultaneously removing by distillation a mixture of methyl acetate/methanol. The reaction being terminated, the excess hydrogen chloride is removed in water jet vacuum at an interior temperature of 70°C. The residue is then submitted to distillation of 0.6 torr. Upon distillation at a temperature of 119°C, 122 g of 2-hydroxyethyl-methyl-thiophosphinic acid-O-isobutyl ester are obtained corresponding to a yield of 81% of the theoretical.

What is claimed is:

1. A process for preparing a 2-hydroxyethanephosphonic acid diester, a 2-hydroxyethyl-phosphinic acid ester, a 2-hydroxyethane-thiophosphonic acid diester or a 2-hydroxyethyl-thiophosphinic acid ester of the formula

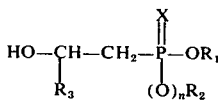

wherein $R_1$ is an alkyl or a substituted alkyl of up to 18 carbon atoms, $R_2$ is an alkyl or a substituted alkyl of up to 18 carbon atoms, a cycloalkyl or a substituted cycloalkyl of up to 10 carbon atoms, an alkenyl or a substituted alkenyl of up to 18 carbon atoms, an aryl or a substituted aryl of up to 14 carbon atoms, or an aralkyl or a substituted aralkyl of up to 15 carbon atoms, $R_3$ is hydrogen, alkyl or substituted alkyl of up to 18 carbon atoms, an alkenyl or substituted alkenyl of up to 18 carbon atoms, a cycloalkyl or substituted cycloalkyl of up to 10 carbon atoms, an aryl or a substituted aryl of up to 14 carbon atoms, or an aralkyl or a substituted aralkyl of up to 15 carbon atoms, X is oxygen or sulfur and $n$ is 0 or 1, which comprises heating at a temperature between about 25°C. and about 150°C. a 2-acyloxy compound of the formula

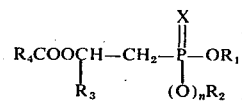

wherein $R_4$ is an alkyl of 1 to 4 carbon atoms, in an alcohol of the formula ROH having 1 to 4 carbon atoms containing from about 0.1 to about 25 mol percent of a strong acid or from about 1 to about 15 mol percent of a strong base, said mol percent being calculated on the basis of said 2-acyloxy compound, to form said ester or diester and an ester of the formula $R_4COOR$, and removing said ester of the formula $R_4COOR$ from the reaction mixture.

2. A process according to claim 1 wherein said temperature is between about 40°C. and about 120°C.

3. A process according to claim 1 wherein said temperature is between about 60°C. and about 90°C.

4. A process according to claim 1 wherein the mol percent of said strong acid is between about 0.5 and about 15 and the mol percent of said strong base is between about 3 to about 7.

5. A process according to claim 1 wherein the mol percent of said strong acid is between about 1 and about 8.

6. A process according to claim 1 wherein said strong acid is HCl, $H_2SO_4$, or p-toluene sulfonic acid and said strong base is NaOH, KOH, sodium methylate or potassium methylate.

7. A process according to claim 1 wherein the molar ratio of said alcohol ROH to said 2-acyloxy compound is between about 3:1 and about 15:1.

8. A process according to claim 1 wherein the molar ratio of said alcohol ROH to said 2-acyloxy compound is between about 6:1 and about 12:1.

9. A process according to claim 1 wherein said alcohol ROH is methanol or ethanol.

10. A process according to claim 1 wherein said alcohol is anhydrous.

11. A process according to claim 1 wherein said ester $R_4COOR$ is removed by distillation.

12. A process according to claim 1 wherein said ester $R_4COOR$ is removed by distillation at reduced pressure.

13. A process according to claim 1 wherein said ester $R_4COOR$ is removed by distillation azeotropically with said alcohol ROH.

14. A process according to claim 1 wherein $R_1$ is an alkyl or substituted alkyl of up to 4 carbon atoms, $R_2$ is an alkyl or substituted alkyl of up to 4 carbon atoms, cyclohexyl or substituted cyclohexyl, alkenyl or substituted alkenyl of up to 4 carbon atoms, phenyl or substituted phenyl, or benzyl or substituted benzyl, $R_3$ is methyl or substituted methyl, cyclohexyl or substituted cyclohexyl, phenyl or substituted phenyl, or benzyl or substituted benzyl, $R_4$ is methyl and said alcohol ROH is methanol or ethanol.

15. A process according to claim 1 wherein said 2-acyloxy compound is a 2-acetoxy compound.

* * * * *